(12) United States Patent
Maruyama

(10) Patent No.: US 8,053,702 B2
(45) Date of Patent: Nov. 8, 2011

(54) METHOD OF CONNECTING PIPE MEMBERS FOR ENDOSCOPE

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 386 days.

(21) Appl. No.: 12/358,351

(22) Filed: Jan. 23, 2009

(65) Prior Publication Data

US 2009/0184095 A1    Jul. 23, 2009

(30) Foreign Application Priority Data

Jan. 23, 2008   (JP) .................................. 2008-012433

(51) Int. Cl.
   *B23K 26/00* (2006.01)
(52) U.S. Cl. .......... 219/121.64; 219/121.63; 219/121.84
(58) Field of Classification Search ............. 219/121.64, 219/212.63, 212.66, 212.65, 121.84, 121.85; 600/101
   See application file for complete search history.

(56) References Cited

U.S. PATENT DOCUMENTS

| | | | |
|---|---|---|---|
| 4,000,392 A * | 12/1976 | Banas et al. ............. | 219/121.63 |
| 4,533,806 A * | 8/1985 | Kawasaki et al. ............. | 219/609 |
| 4,684,779 A * | 8/1987 | Berlinger et al. ........ | 219/121.64 |
| 4,723,064 A * | 2/1988 | Bothe, II .................. | 219/121.84 |
| 5,001,323 A * | 3/1991 | Matsutani et al. ....... | 219/121.63 |
| 5,840,015 A | 11/1998 | Ogino | |
| 5,864,111 A * | 1/1999 | Barefoot ......................... | 219/61 |
| 5,977,513 A * | 11/1999 | Findlan ..................... | 219/121.64 |
| 2002/0017515 A1* | 2/2002 | Obata et al. ............... | 219/137 R |
| 2006/0155271 A1 | 7/2006 | Sugita et al. | |
| 2006/0271066 A1* | 11/2006 | Kimura et al. ................. | 606/108 |
| 2007/0043324 A1 | 2/2007 | Shibata et al. | |
| 2007/0203487 A1 | 8/2007 | Sugita | |
| 2007/0236782 A1 | 10/2007 | Sano | |
| 2007/0282326 A1 | 12/2007 | Sugita | |

FOREIGN PATENT DOCUMENTS

JP   4-25007   4/1992
JP   2003-33320   2/2003

OTHER PUBLICATIONS

English language Abstract of JP 2003-33320, Feb. 4, 2003.
U.S. Appl. No. 12/354,910, filed on Jan. 16, 2009.

* cited by examiner

*Primary Examiner* — M. Alexandra Elve

(74) *Attorney, Agent, or Firm* — Greenblum & Bernstein, P.L.C.

(57) ABSTRACT

A method for connecting pipe members for an endoscope includes the steps of arranging two pipe members each made of a corrosion-resistant alloy material by fitting one in another so that a passage is defined through the two pipe members, jetting inert gas toward an exterior of an area at which the two pipe members are to be connected, injecting inert gas through the passage defined through the two pipe members, and connecting the two pipes by laser welding such that a laser beam is irradiated toward the exterior of the area at which the two pipe members are to be connected with jetting the inert gas toward the exterior of the area at which the two pipe members are to be connected and injecting the inert gas through the passage defined by through the two pipe members.

15 Claims, 3 Drawing Sheets

METHOD OF CONNECTING PIPE MEMBERS FOR ENDOSCOPE

BACKGROUND OF THE INVENTION

1. Technical Field

The present invention relates to a method of connecting pipe members for an endoscope.

2. Related Art

Generally, pipe members used for endoscopes are made of corrosion-resistant alloy materials, and pipe members are connected by welding or silver-alloy brazing and the like to have a watertight structure. In recent years, laser beam irradiation so-called laser welding has been used in view of easiness of operation and steadiness of welding. An example of such a configuration is disclosed in Japanese Patent Provisional Publication No. HEI 4-25007.

When laser welding is performed, a connection area irradiated with a laser beam tends to be unnecessarily oxidized due to increase of temperature. In such a case, the connection strength may be largely lowered.

SUMMARY OF THE INVENTION

The above oxidation phenomenon occurs also in a passage in pipe members as connected. In particular, the oxidation phenomenon notably occurs when the thickness of the wall of the pipe members is thin. Once the pipe passage is oxidized, such oxidized portions may be peeled off when liquids and/or gases are passed through the pipe passage during endoscopic diagnosis and left inside the human body. Further, filthy liquids and the like from human body may be stuck in the oxidized area and accumulated. Then, oxidation of the pipe members may be progressed due to existence of such filthy materials.

The present invention is advantageous in that there is provided an improved method of connecting pipe members for an endoscope. According to the method, oxidization of the pipe passage inside the two pipe members, which are connected by laser welding, can be prevented and therefore occurrence of the above-described problems can be prevented in advance.

According to aspects of the invention, there is provided a method for connecting pipe members for an endoscope. The method includes the steps of arranging two pipe members each made of a corrosion-resistant alloy material by fitting one in another so that a passage is defined through the two pipe members, jetting inert gas toward an exterior of an area at which the two pipe members are to be connected, injecting inert gas through the passage defined through the two pipe members, and connecting the two pipes by laser welding such that a laser beam is irradiated toward the exterior of the area at which the two pipe members are to be connected with jetting the inert gas toward the exterior of the area at which the two pipe members are to be connected and injecting the inert gas through the passage defined by through the two pipe members.

According to aspects of the present invention, pipe members are connected by the laser welding. During irradiation of the laser beam, an inert gas is jetted toward the connection area to which a laser beam is irradiated for laser welding from outside and inside. Therefore, the oxidation can be suppressed during the laser welding.

BRIEF DESCRIPTION OF THE ACCOMPANYING DRAWINGS

DETAILED DESCRIPTION OF THE EMBODIMENTS

Hereinafter, referring to accompanying drawings, embodiments of the present invention will be described. An example of an endoscope having a pipe connection structure, to which the embodiments of the invention are applicable, is U.S. Pat. No. 5,840,015, teachings of which are incorporated herein by reference.

Figure 1:
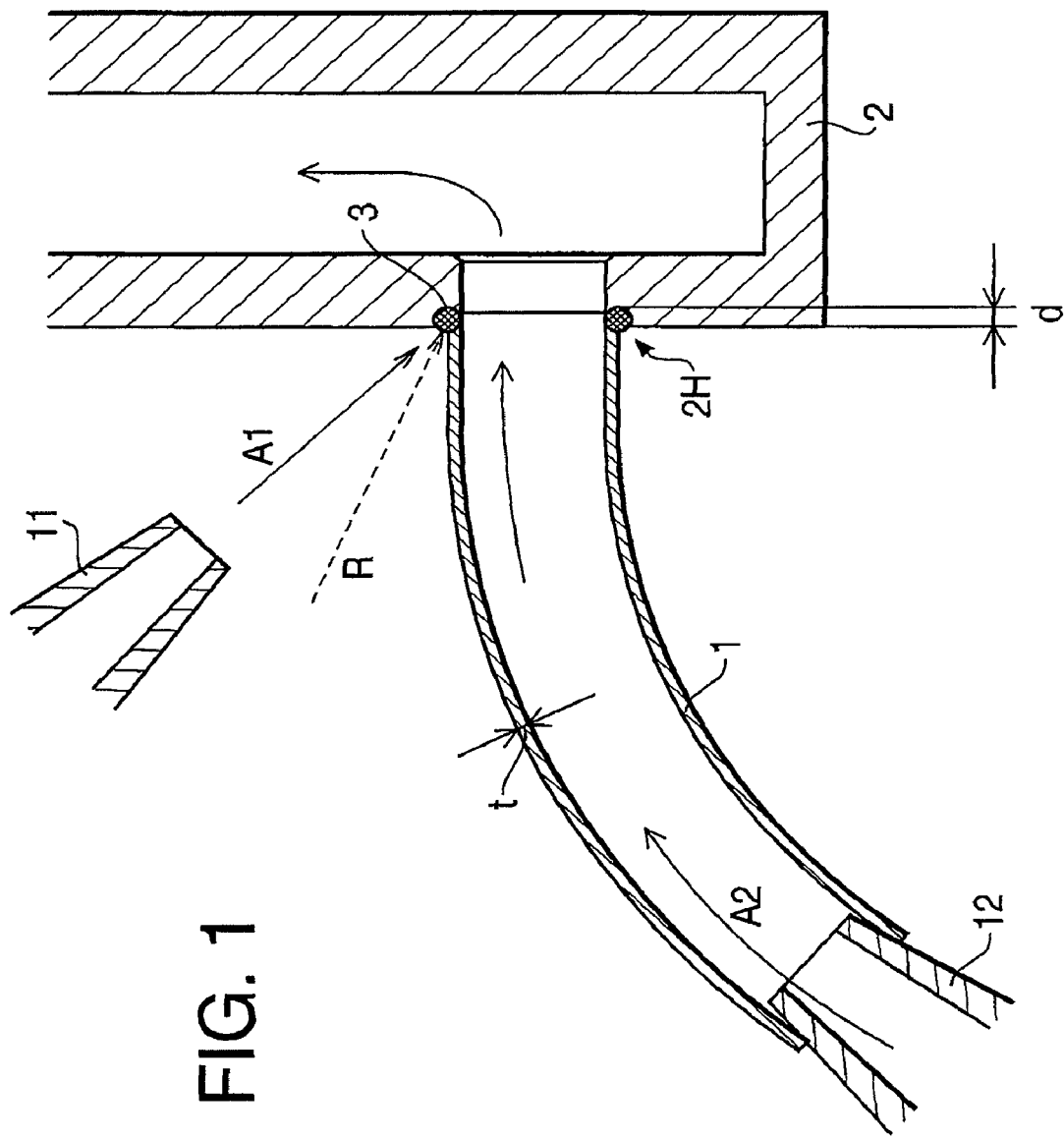
FIG. 1 is a cross sectional side view showing a condition where pipe members for an endoscope are connected according to a first embodiment of the invention.

FIG. 1 shows a condition where a first pipe member 1 and a second pipe member 2 used for an endoscope are connected. Each of the first and second pipe members 1 and 2 is made of a corrosion-resistant alloy material such as stainless steel (e.g., SUS 304), and the first pipe member 1 is formed in the shape of a pipe with a thin wall, while the second pipe member 2 is formed in the shape of a cylinder.

One end of the first pipe member 1 is fitted in a pipe insertion hole 2H formed on the second pipe member 2. Then a laser beam R is irradiated on the entire circumference of the exterior of the connected area, whereby the first pipe member 1 and the second pipe member 2 are welded (seam welding is done). In FIG. 1, a reference numeral 3 denotes the welded area. Thus, a pipe passage is defined in the first and second pipe members 1 and 2 in a communicated manner.

According to the above method, a fitted length d, along the axis of the first pipe member 1, with respect to the insertion hole 2H formed on the second pipe member 2 is set in a range of 0.5 to 2 times the wall thickness t of the first pipe member 1. With this structure, the laser welding can be performed solidly without leaving a gap in the fitted area, after welding.

When the first pipe member 1 and the second pipe member 2 are irradiated with the laser beam R for welding, inert gas A1, such as Argon gas, is jetted from a first inert gas jet nozzle 11 toward the inner surfaces of the connected portion of the first and second pipe members 1 and 2, whereby oxidation of the surface of their laser-welded area 3 is prevented.

At the same time, inert gas A2, such as Argon gas, is jetted from a second inert gas jet nozzle 12, which is connected to the outer end of the first pipe member 1. The inert gas A2 passes through the pipe passage in the first and second pipe members 1 and 2, whereby oxidation of inner side of the laser welding area 3 in the pipe members 1 and 2 is prevented. As described above, according to the above method, occurrence of various problems can be prevented.

In the above method, the inert gas A2 is passed through the pipe passage defined by the first and second pipe members 1 and 2 at a normal temperature (approximately in the range of 0 to 40° C.), and the pressure of the inert gas A2 is approximately in a range of 0.05 to 0.5 MPa. Therefore, according to the above described method, an antioxidation effect can be achieved under practical operational conditions.

Figure 2:
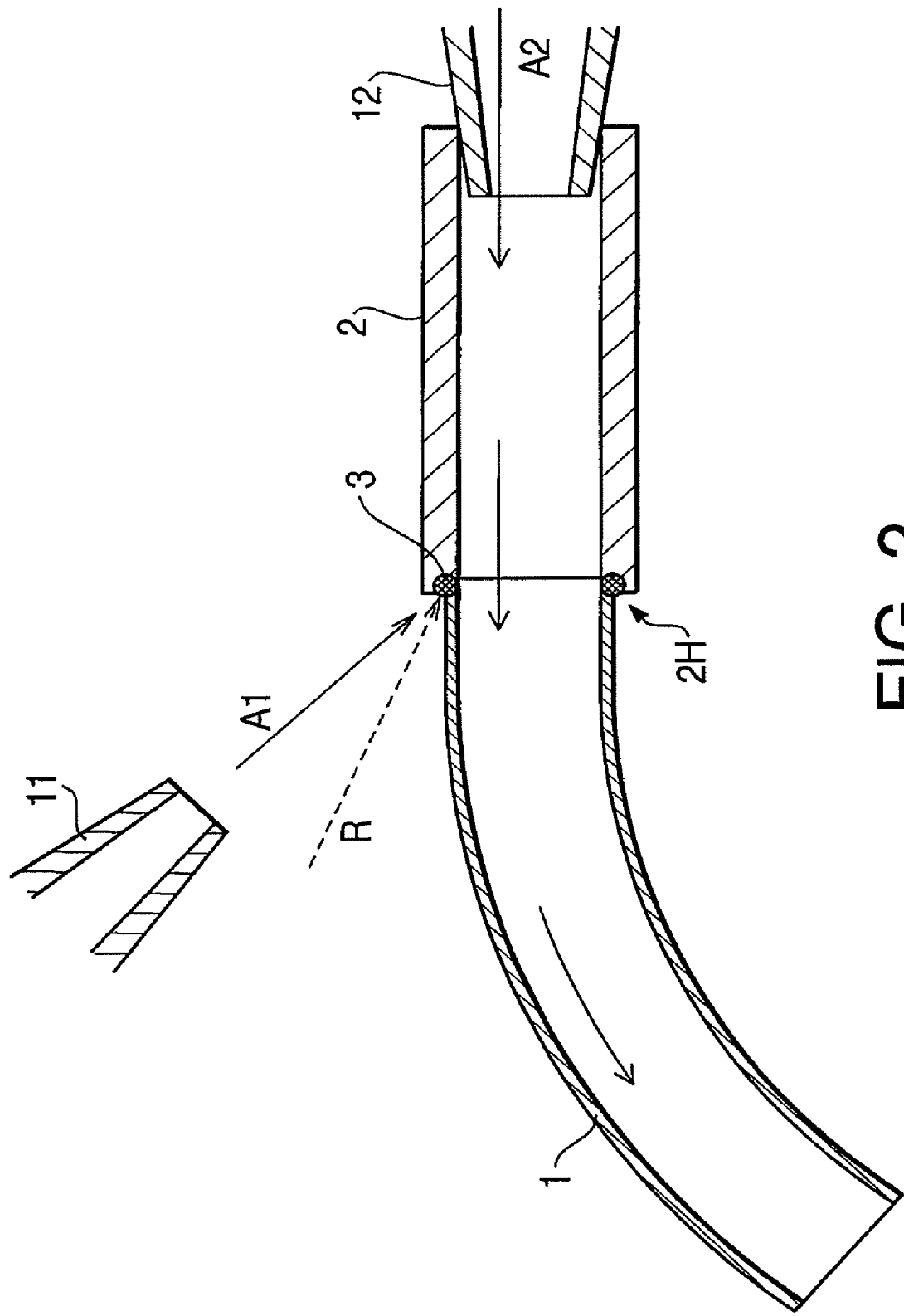
FIG. 2 is a cross sectional side view showing a condition where pipe members for an endoscope are connected according to a second embodiment of the invention.

FIG. 2 shows a second embodiment according to an aspect of the invention, and it differs from the first embodiment in that following points. That is, the second pipe member 2 is formed in the shape of a thick walled cylinder. The first pipe member 1 is connected to one end of the second pipe member 2, and the second inert gas jet nozzle 12 is connected to the other end of the second pipe member 2. With this configuration, the effects similar to those of the first embodiment can be achieved.

Figure 3:
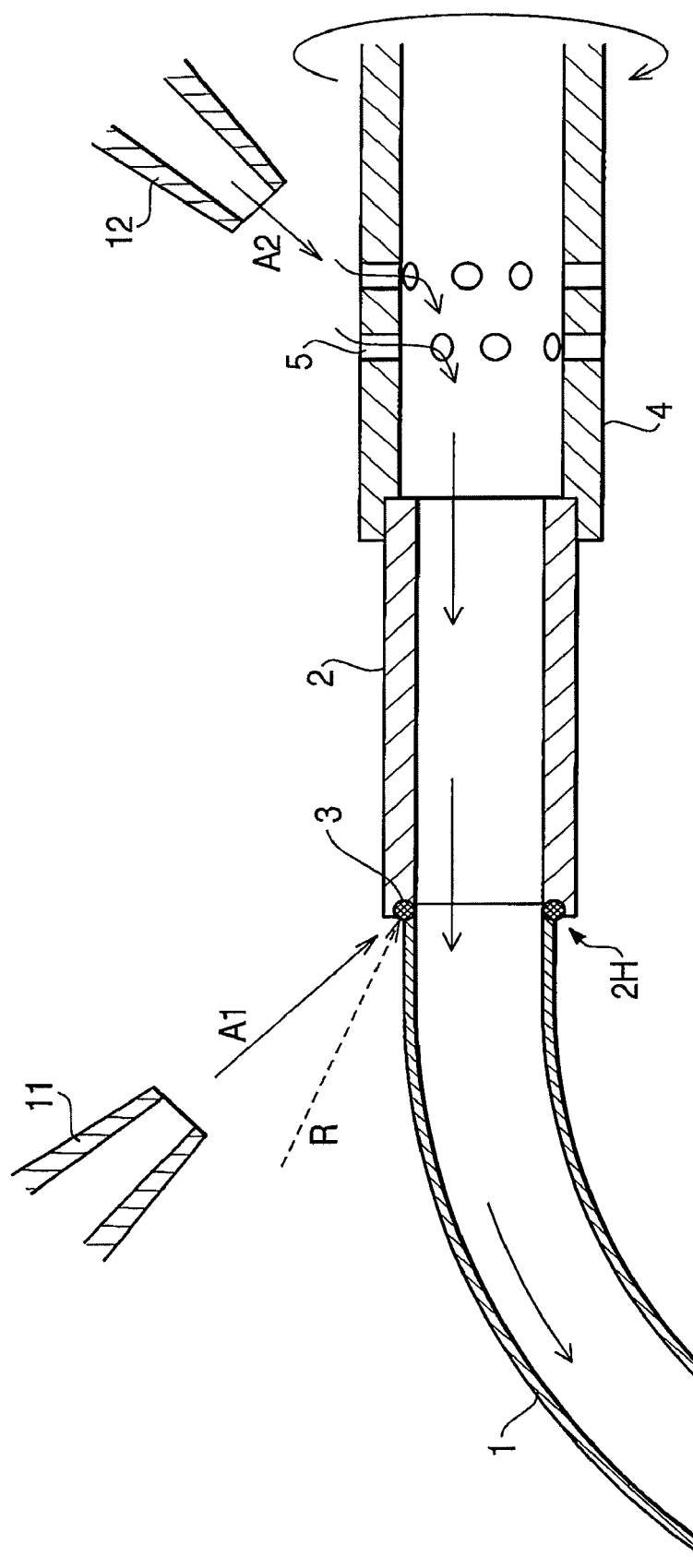
FIG. 3 is a cross sectional side view showing a condition where pipe members for an endoscope are connected according to a third embodiment of the invention.

FIG. 3 shows a third embodiment according to an aspect of the invention. According to the third embodiment, the first and second pipes 1 and 2 are to be connected as in the second embodiment. In the third embodiment, instead of inserting the second inert gas jet nozzle 12 in the end of the second pipe 2, there is provided an inert gas injection jig 4 having a cylindrical body, which is formed with a plurality of through-holes 5 perforated on the circumferential wall thereof, is connected to the end of the second pipe member 2. The second inert gas jet nozzle 12 is arranged outside the inert gas injection jig 4 as shown in FIG. 3. Specifically, the inert gas injection jig 4 is arranged to point toward the through-holes 5 from outside of the inert gas injection jig 4.

The first pipe member 1, the second pipe member 2, and the inert gas injection jig 4 are rotated around the axis of the inert gas injection jig 4 in an integrated manner, and consequently, the inert gas A2 brought through the through-holes 5 into the inert gas injection jig 4 passes through the pipe passage defined in the first and second pipe members 1 and 2. The first inert gas jet nozzle 11 is arranged in a manner similar to the second embodiment. The laser beam R is also irradiated in a manner similar to the second embodiment. According to the above method, the effects similar to those of the first and the second embodiments can be achieved.

The present invention is not to be limited to the embodiments described above, and further aspects or modifications may be adopted. For example, both of the two pipe members 1 and 2 may be not always thin-walled pipes. And, the inert gases A1 and A2 may also be any inert gases other than Argon gas.

The present disclosure relates to the subject matter contained in Japanese Patent Application No. 2008-012433, filed on Jan. 23, 2008, which is expressly incorporated herein by reference in its entirety.

What is claimed is:

1. A method for connecting pipe members for an endoscope, comprising:
   arranging two pipe members, each pipe member comprising a corrosion-resistant alloy material, by fitting one pipe member into the other pipe member so that a passage is defined through the two pipe members;
   jetting an inert gas toward an exterior of an area at which the two pipe members are to be connected;
   injecting an inert gas through the passage defined through the two pipe members concurrently with the jetting; and
   connecting the two pipe members by laser welding such that a laser beam is irradiated toward the exterior of the area at which the two pipe members are to be connected, together with the jetting of the inert gas toward the exterior of the area at which the two pipe members are to be connected and with the injecting of the inert gas through the passage defined through the two pipe members.

2. The method according to claim 1, wherein the injecting of an inert gas includes connecting an inert gas jet nozzle to an end of one of the two pipe members.

3. The method according to claim 1, wherein the injecting an inert gas includes:
   connecting an inert gas injection jig, which has a cylindrical body provided with a plurality of perforations on the circumferential wall of the cylindrical body, to an end of one of the two pipe members; and
   jetting an inert gas through the plurality of perforation of the inert gas injection jig, the inert gas jetted in the inert gas injection jig passing through the pipe passage defined in the two pipe members.

4. The method according to claims 1, wherein the pressure of the inert gas to be passed through the pipe passage is in a range of 0.05 to 0.5 mpa.

5. The method according to claim 1, wherein the temperature of the inert gas to be passed through the pipe passage is in a range of 0 to 40° C.

6. The method according to claim 1, wherein the inert gas to be passed through the pipe passage is argon gas.

7. The method according to claim 1, wherein at least one of the two pipe members has a cylindrical wall with open ends.

8. The method according to claim 1, the injecting of the inert gas through the passage comprises injecting the insert gas into a passage defined by interior surfaces of the two pipe member which are not irradiated by the laser beam.

9. The method according to claim 1, the area of the pipes onto which the laser beam is irradiated is the same as an area towards which the inert gas is jetted.

10. The method according to claim 1, the injecting of the inert gas through the passage defined through the two pipe members comprises injecting the inert gas through a passage defined by the inner surfaces of the two pipe members opposite to a surface which is exposed to irradiation by the laser beam.

11. The method according to claim 1, the irradiation of the laser beam and the jetting of the inert gas are both directed to a same exterior portion of the pipe members.

12. The method according to claim 1, wherein the laser welding comprises seam welding.

13. The method according to claim 1, wherein an end portion of a first one of the pipe members is fitted into a hole on the second pipe member, and a length, along the axis of the first pipe member, that extends into the hole of the second pipe member is within a range of 0.5 to 2 times a wall thickness of the first pipe member.

14. The method according to claim 1, wherein an end portion of a first one of the pipe members is fitted into an end portion of a second one of the pipe members.

15. The method according to claim 3, wherein the pipe members and the inert gas injection jig are rotated about an axis of the inert gas injection jig.

* * * * *